United States Patent [19]

Elkins

[11] 4,308,028

[45] Dec. 29, 1981

[54] DEVICE AND METHOD FOR THE CHEMICAL TESTING AND MICROSCOPIC EXAMINATION OF LIQUID SPECIMENS

[76] Inventor: Carlos D. Elkins, 1414 S. Fairplain Ave., Whittier, Calif. 90601

[21] Appl. No.: 139,681

[22] Filed: Apr. 14, 1980

[51] Int. Cl.$^3$ .................. G01N 1/10; G01N 21/11; G01N 21/78; G01N 33/52

[52] U.S. Cl. .................. 23/230 B; 73/864.02; 73/864.72; 356/246; 422/55; 422/56; 422/58; 422/100; 422/101; 422/102

[58] Field of Search .................. 23/230 B; 422/55, 56, 422/58, 59, 100, 101, 102; 356/244, 246; 73/864.02, 864.72

[56] References Cited

U.S. PATENT DOCUMENTS

| | | | |
|---|---|---|---|
| 3,198,064 | 8/1965 | Moore | 356/244 |
| 3,607,098 | 9/1971 | Strande | 422/102 |
| 3,814,522 | 6/1974 | Clark et al. | 422/102 X |
| 3,905,702 | 9/1975 | Johnson | 356/246 X |
| 4,022,576 | 5/1977 | Parker | 422/73 X |
| 4,088,448 | 5/1978 | Lilja et al. | 356/246 X |
| 4,160,008 | 7/1979 | Fenocketti et al. | 422/56 |

FOREIGN PATENT DOCUMENTS 2649002  5/1978  Fed. Rep. of Germany .... 23/230 B

*Primary Examiner*—Arnold Turk
*Attorney, Agent, or Firm*—Edgar W. Averill, Jr.

[57] ABSTRACT

A device for facilitating the microscopic and/or spectrophotometric viewing of liquid specimens. The device is an elongated strip having a chamber at one end. The chamber is formed by two generally parallel transparent flat sheets. The device is held by a supporting disc or plug which has a slot or chamber formed for insertion of the strip. The strip with its surrounding disc or plug is inserted in a test tube which has a disc-supporting shoulder formed near the bottom thereof. The disc or plug traps a certain amount of liquid below the shoulder near the bottom of the test tube.

29 Claims, 28 Drawing Figures

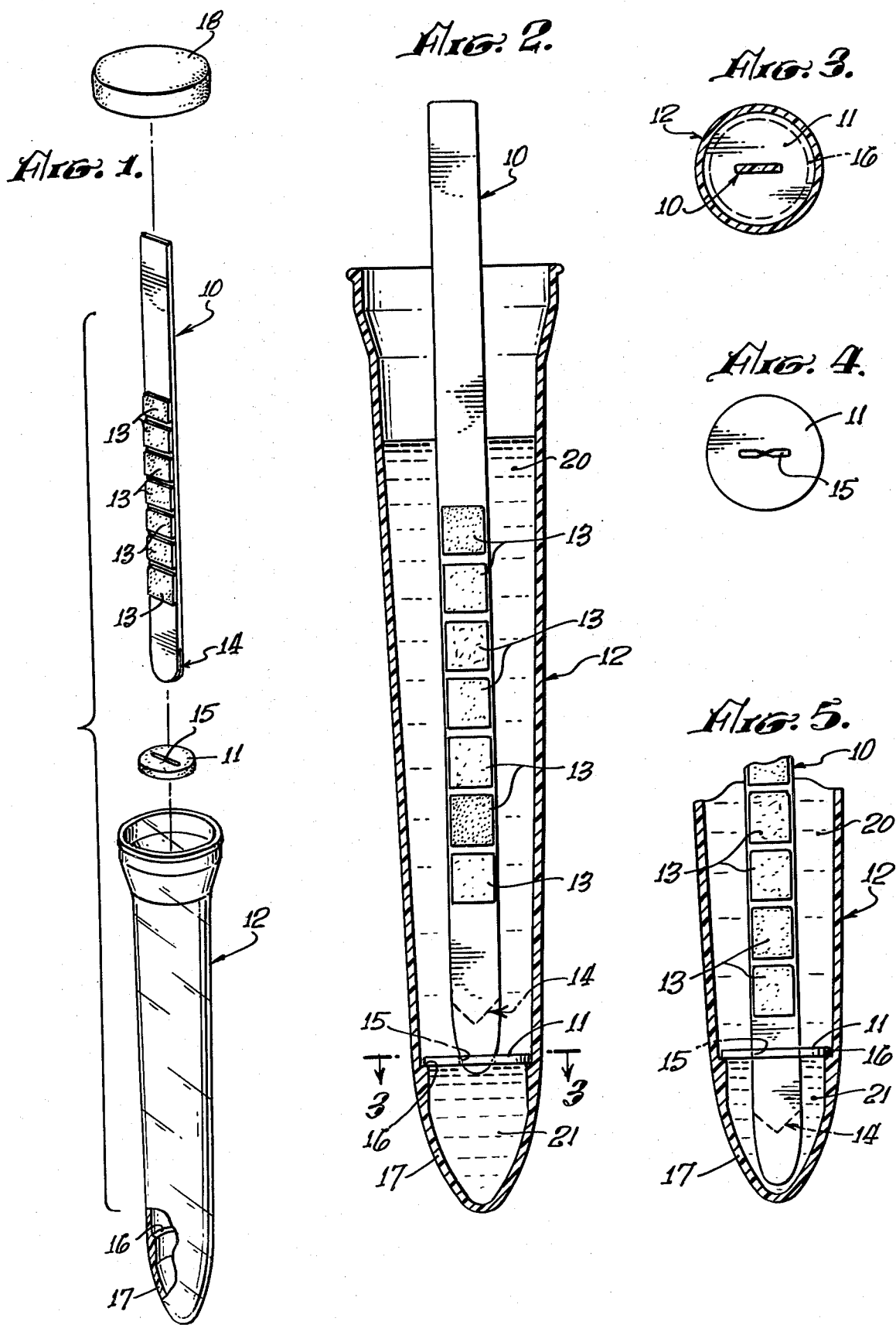

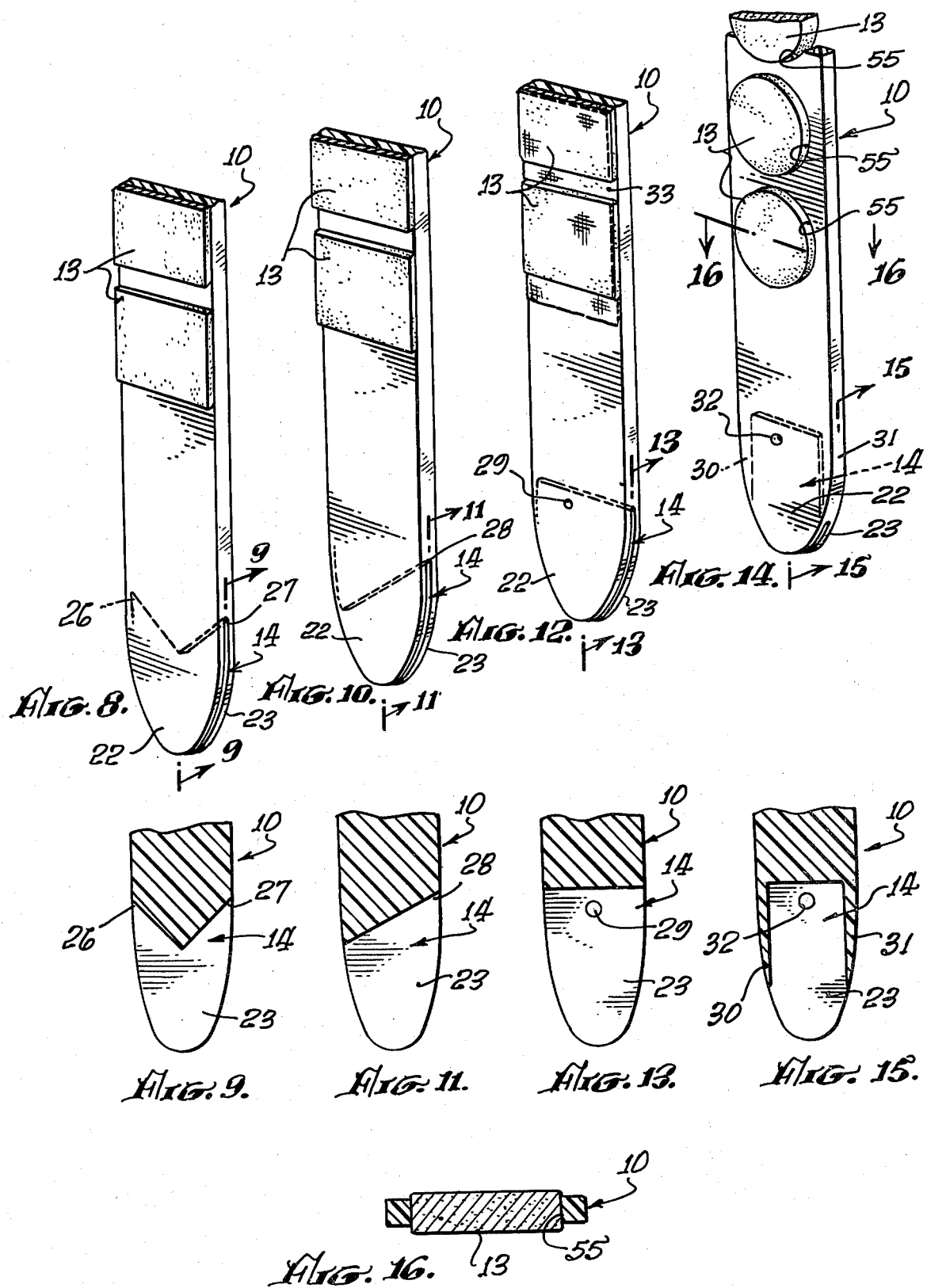

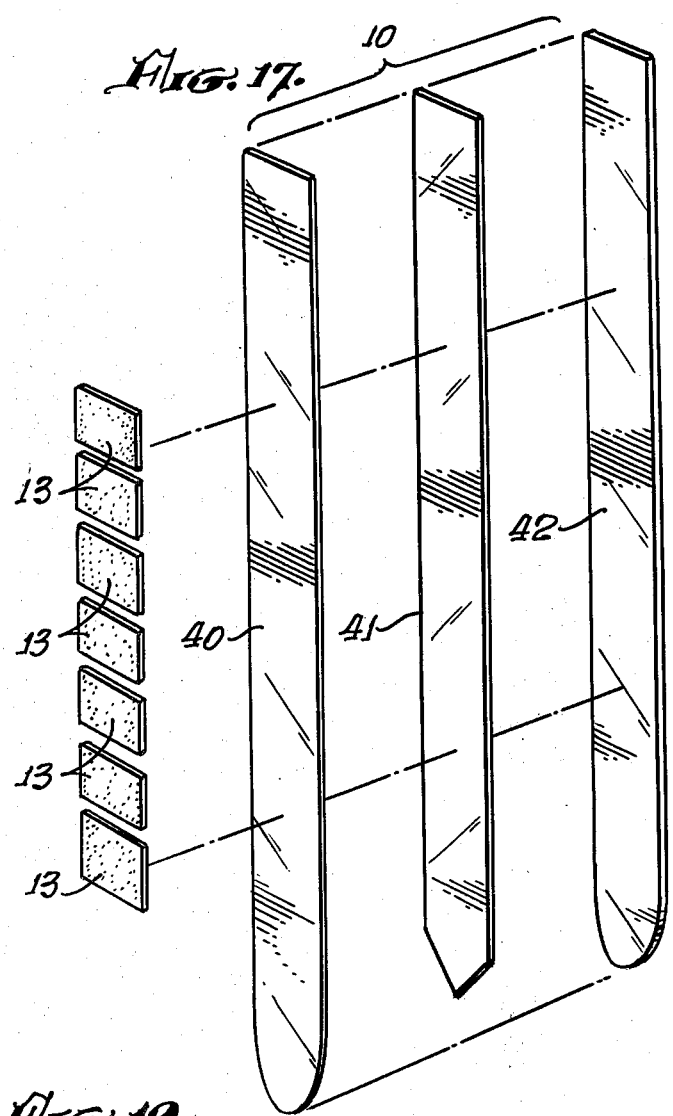
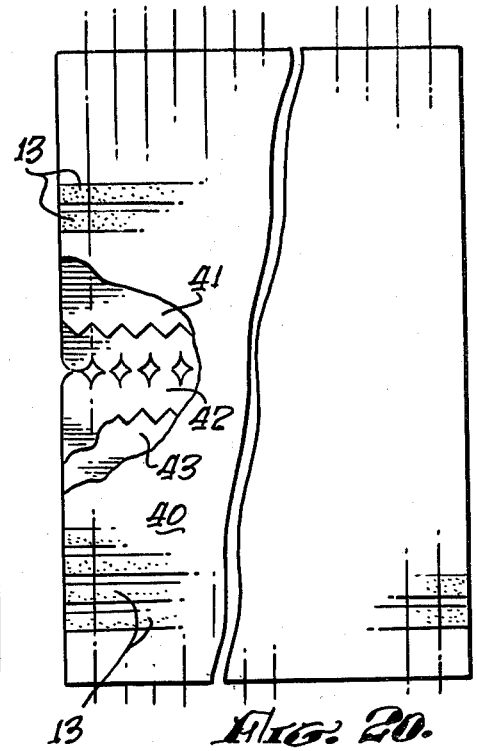
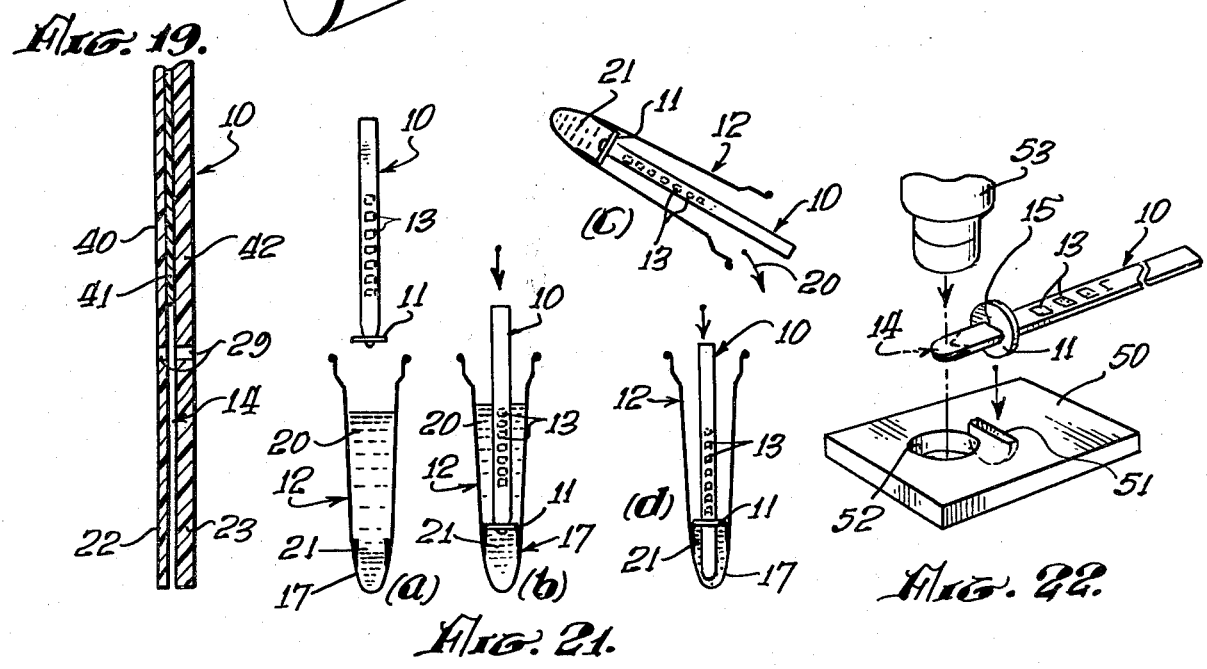

4,308,028

DEVICE AND METHOD FOR THE CHEMICAL TESTING AND MICROSCOPIC EXAMINATION OF LIQUID SPECIMENS

BACKGROUND OF THE DISCLOSURE

The field of the invention is laboratory apparatus, and the invention relates more specifically to devices for facilitating the microscopic or spectrophometric viewing of liquid specimens. Liquid specimens are typically viewed by placing a drop of the specimen on a transparent glass or plastic slide and covering the drop with a thin square cover slip. The cover slip spreads the liquid drop into a thin flat layer appropriate for viewing.

In certain microscopic evaluations, it is important to simplify and speed up the above-mentioned method, and this is especially true for repetitive tests such as carried out in hospital laboratories for blood or urine analysis. One particularly effective method is referred to under the trademark "kova" system which is described in applicant's U.S. Pat. No. 3,777,283. In the "Kova" system there described, a drop of the specimen is placed on a platform and drawn by capillary action into a chamber which spreads the liquid into a thin generally flat film appropriate for microscopic examination.

While the above described improved system has found wide-spread acceptance, it is nonetheless capable of further improvement. For instance, in the microscopic evaluation of a urine specimen, it is common practice to centrifuge a sample and to then draw a sample from the bottom of the centrifuged specimen which would be highly concentrated in any particulate matter and to then view this concentrated sample under a microscope. One technique for obtaining a sample from the bottom of a centrifuged specimen involves the use of a dropper with an elastic bulb on the top thereof which is inserted in the test tube so that the sample may be drawn from the bottom of the test tube. While the drop of such material may be readily placed on the platform, this does require a separate handling step which, in turn, gives rise to two potential sources of error or contamination namely, in the event that the dropper is contaminated, the reading would be in error and in the event the drop is placed in the wrong compartment, the sample would be reported incorrectly.

Thus, a method which reduces the handling of a centrifuged specimen and also reduces the possibility of unintentional interchanging of samples is needed. Furthermore, a method which eliminates the need for a separate dropper would not only reduce the possibility of cross-contamination but would also provide a less expensive analytical method.

Another test which is commonly run on samples of urine utilizes a plurality of reagent pads adhered to a single carrier strip. One such strip is sold under the trademark "Chemstrip" by Bio-Dynamics Division of Mannheim-Boehringer. Another strip is sold under the trademark "Multistix" by Ames Company, Division Miles Laboratories, Inc. In both instances, a plurality of reagent areas are placed on a single strip and the reagent areas are treated with different colormetric dyes which change color in the presence of various substances. For instance, one strip would provide a pH test, another would provide a protein test, a third, a glucose test, a fourth, a ketone test, a fifth, a bilirubin test, a sixth, a blood test, a seventh, a nitrite test and the eighth, a urobilinogen test. This colormetric test, while being a highly efficient method for running many tests at one time, has one disadvantage and that is the possibility of mislabling or interchanging of samples. A method which reduces the possibility of this error is needed.

SUMMARY OF THE INVENTION

The present invention is for an apparatus including an elongated strip for facilitating the microscopic viewing of liquid specimens. The elongated strip has a chamber at its lower extremity. The chamber is formed by two generally parallel, transparent, flat members. A strip support member which may be a disc or plug having a slot or chamber formed therein for insertion of the lower extremity of the elongated strip is used to support the strip and the slot or chamber is small enough so that the strip support member is firmly held by the strip after the strip is inserted therein. A test tube having a disc or plug supporting shoulder is utilized with the strip and disc of the present invention. After a sample has been placed in the test tube and centrifuged, the elongated strip having a strip-support member supported thereby is inserted into the test tube so that the member rests against the shoulder of the test tube. The liquid above the support member and shoulder may then be decanted from the test tube and the bottom part of the centrifuged specimen may be agitated and mixed by striking the bottom of the tube with a finger. This agitation action mixes the particulate matter in the bottom chamber. The strip is then pushed downwardly and the chamber fills by capillary action thereby providing a concentrated sample of the particulate matter for microscopic or spectrophotometric evaluation. As the strip is removed from the test tube, the chamber remains full by capillary action. In a preferred embodiment, the disc, or plug is placed in a recess which holds both the disc or plug and the strip in a position for easy viewing by microscope. In a still further improved version, the slot in the strip-supporting disc is shaped to decrease the size of the chamber and void the chamber of a majority of the liquid contained therein as it is inserted through the slot and then caused to open after the chamber has been inserted completely through the slot. In an alternate embodiment a thin, waterproof plastic film is positioned below the disc and serves to keep the chamber empty until the strip is pushed downwardly to the bottom of the test tube. In another embodiment, a plug has a chamber which is closed at the bottom. After decanting, the strip is pushed downwardly and penetrates the bottom of the plug thereby permitting the chamber to be filled with the concentrated sample.

BRIEF DESCRIPTION OF THE DRAWINGS

FIG. 1 is an exploded perspective view of the strip, disc and test tube of the present invention.

FIG. 2 is an enlarged cross-sectional side elevation of the device of FIG. 1.

FIG. 3 is a cross-sectional view taken along line 3—3 of FIG. 2.

FIG. 4 is a top plan view analogous to FIG. 3 of an alternate embodiment of the disc of the strip of the present invention.

FIG. 5 is a fragmentary, cross-sectional view of the lower portion of the strip, disc and test tube of the present invention.

FIG. 8 is an enlarged perspective view partly broken away of the lower portion of the strip of the present invention.

FIG. 9 is a cross-sectional side elevation taken along line 9—9 of FIG. 8.

FIG. 10 is an enlarged fragmentary perspective view of the lower portion of the strip of the present invention.

FIG. 11 is a cross-sectional side elevation taken along line 11—11 of FIG. 10.

FIG. 12 is an enlarged perspective fragmentary view of the lower portion of the strip of the present invention.

FIG. 13 is a cross-sectional side elevation taken along line 13—13 of FIG. 12.

FIG. 14 is an enlarged fragmentary perspective view of the lower portion of an alternate embodiment of the strip of the present invention.

FIG. 15 is a cross-sectional side elevation taken along line 15—15 of FIG. 14.

FIG. 16 is a cross-sectional plan view taken along line 16—16 of FIG. 14.

FIG. 17 is an exploded perspective view of the strip of FIG. 1.

FIG. 18 is a cross-sectional plan view of the strip of FIG. 1.

FIG. 19 is a cross-sectional side elevation of the lower portion of the strip of FIG. 12.

FIG. 20 is a plan view of a plurality of strips of the present invention prior to cutting the same from a sheet.

FIG. 21 is a schematic side elevation showing the operation of the strip, disc and test tube of the present invention.

FIG. 22 is a perspective view of the strip and disc of the present invention together with a jig and microscope showing its use with a microscope.

DESCRIPTION OF THE PREFERRED EMBODIMENTS

Figure 6:
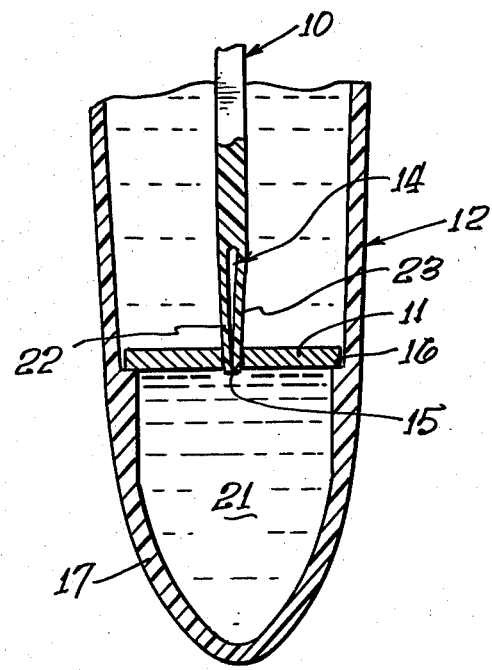
FIG. 6 is a fragmentary enlarged cross-sectional view of a portion of the test tube, the disc and the lower portion of the strip of the present invention.

The device of the present invention is shown in perspective view in FIG. 1 where the strip is indicated by reference character 10, the disc by reference character 11 and the test tube by reference character 12. The strip has a plurality of reagent pads 13 which are of a conventional nature. Typically, the reagent pads provide a quick chemical test for pH, protein, glucose, ketone, bilirubin, blood, nitrite and urobilinogen. Such pads are described in detail in U.S. Pat. Nos. 3,802,842; 3,418,079; 3,585,001; 3,897,214 and 3,232,710. Such pads are typically adhered or otherwise held to a thin plastic strip which is dipped in the sample to be tested. By color changes, the above tests may be quickly performed. In the past, such tests have been a separate procedure in the evaluation of the specimen.

Returning to FIG. 1, strip 10 has a chamber 14 described in more detail below. Briefly, however, chamber 14 is a thin, flat opening between transparent sheets, and chamber 14 holds a liquid sample by capillary action after strip 10 is withdrawn from the liquid sample.

Strip 10 is inserted through the slot 15 of disc 11 and after partial insertion therein, the strip and disc are inserted in test tube 12 so that disc 11 rests on shoulder 16 as shown best in FIG. 2 of the drawings. For most test procedures, a sample of liquid such as a urine sample is placed into test tube 12 and the test tube is centrifuged to cause the concentration of any particulate matter in the bottom portion 17 of test tube 12. Further details of the procedure will be discussed below in reference to FIG. 21 of the drawings.

The device of the present invention may also be used to transport a specimen and thereby eliminate another liquid transfer step and source of error. A cap 18 may be used to cover the opening of test tube 12 before strip 10 is inserted therein.

It is the particulate matter which is of interest for further evaluation by microscopic viewing or by spectrophotometric evaluation. In the past, the sample is centrifuged and the bottom portion of the centrifuged sample is agitated and a sample collected from the bottom of the tube. This has been carried out by the provision of a hollow tube with a widened portion which is inserted in the centrifuged sample, and an elastic bulb is squeezed to both agitate the liquid and solid at the bottom of the tube and also to draw in the small sample for placing on a microscope slide.

The device of the present invention is capable of collecting a sample from the bottom of the test tube without the necessity of a separate sampling device. The device and method of the present invention eliminates one transfer step namely, that of transfering the sample from the test tube to the microscope slide. This step constitutes a possible source of error in that the sample could be mislabled or placed on the wrong microscope slide. In spite of the care exercised by most medical technologists, with the very large number of samples tested by most hospitals even a very low percentage of error can be significant and any device which reduces a potential error causing step is beneficial.

Figure 7:
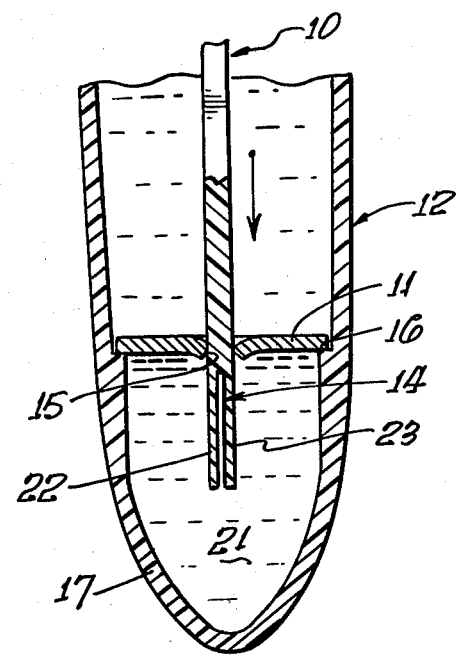
FIG. 7 is a fragmentary enlarged cross-sectional view of a portion of the test tube, the disc and the lower portion of the strip of the present invention.

The disc used in conjunction with the present invention is shown in enlarged plan view in FIG. 3. Disc 11 is resting against shoulder 16 of test tube 12. The slot 15 is generally rectangular in shape and is small enough so that it firmly holds strip 10 so that when strip 10 is withdrawn from test tube 12, it remains affixed at its position as shown in FIG. 5 of the drawings. Disc 11 performs the function of providing a waterproof barrier so that the upper portion of the sample (indicated by reference character 20) may be poured out of test tube 12 while the lower portion 21 is held below disc 11. This is shown best in FIG. 21 of the drawings. After the sample has been decanted, the lower portion of the specimen is agitated to mix the particulate matter with the liquid portion of the sample. This may be done readily by flicking the bottom of the test tube with an index finger. Rather than being poured out, the upper portion of the sample may be drawn off by vacuum. Furthermore, the slot 15 of disc 11 tends to evacuate the chamber 14 so that chamber 14 is open so that the majority of liquid in the chamber is taken from the lower portion 21 of the specimen. This evacuating action is shown best in FIGS. 6 and 7 of the drawings where it can be seen that chamber 14 is reduced in size by a squeezing action of slot 15 on the outer edges 22 and 23 of chamber 14. As shown in FIG. 7, after chamber 14 has passed slot 15, it is again fully opened and the sample consists of a part of the lower portion 21 of the specimen thus it contains a concentrated amount of particulate matter as compared to the original specimen.

Figure 23:
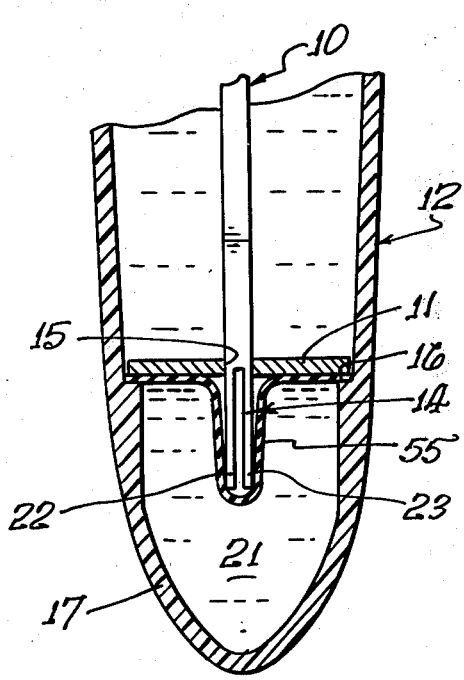
FIG. 23 is a fragmentary cross-sectional side elevation of an alternate embodiment of the strip, disc and test tube of the present invention.
Figure 24:
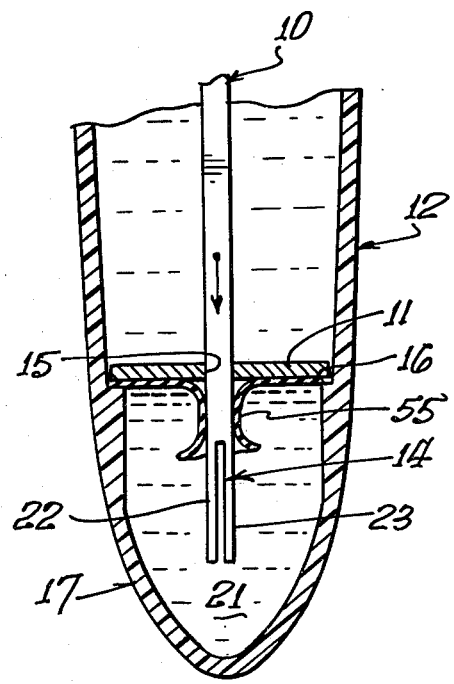
FIG. 24 is a fragmentary cross-sectional side elevation of the alternate embodiment of the strip, disc and test tube of FIG. 23.
Figure 25:
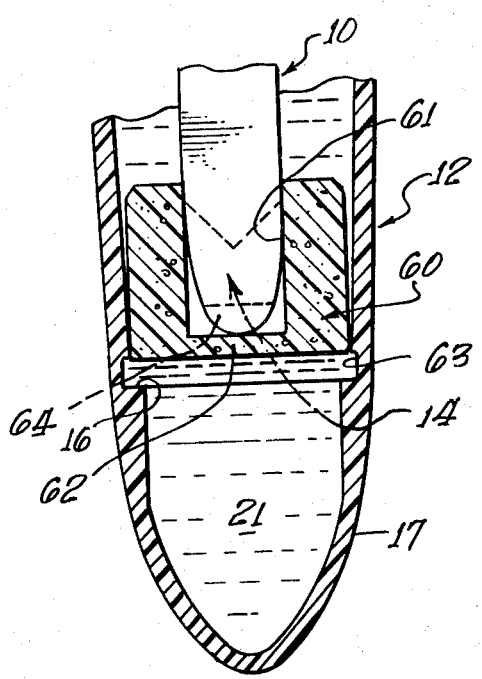
FIG. 25 is a fragmentary, cross-sectional side elevation of the lower portion of the test tube and strip of the present invention utilizing a plug in place of the disc of FIG. 1 through 24.

An alternate shape of disc 11 is shown in FIG. 4 where slot 25 is narrowed in the center to further deform outer edges 22 and 23 of chamber 14. This narrowed portion further assists in the holding of disc 11 in its proper position (as shown in FIG. 5) about strip 10. An alternate shape of disc 11 is shown in FIGS. 23 and 24. In this embodiment, disc 11 has a barrier layer 55 on the lower surface thereof. Barrier layer 55 may be made from a thin plastic sheet which is ruptured by insertion of strip 10 therethrough. Barrier layer 55 keeps chamber 14 empty until it enters the lower portion 21 of the specimen. Barrier layer 55 could alternately be made from a thin frangible material. Barrier layer 55 is preferably sufficiently below disc 11 so that chamber 14 is below the upper surface of disc 11 whereby chamber 14 is empty until layer 55 is penetrated. If a barrier layer 55 is utilized, then it is not necessary that one or both of the side walls of chamber 14 be flexible.

An alternate embodiment of the present invention is shown in FIGS. 25, 26, 27 and 28 where a plug is used in place of the disc 11. The plug 60 is shown in perspective view in FIG. 28 and in cross-sectional view in FIGS. 25, 26 and 27. Plug 60 has a recess 61 into which the chamber 14 of strip 10 is inserted as shown best in FIG. 25. Recess 61 may have a floor 62 which prevents the entry of liquid into recess 61. The sidewalls of recess 61 are fabricated so that they closely touch the outer walls of strip 10.

Figure 26:
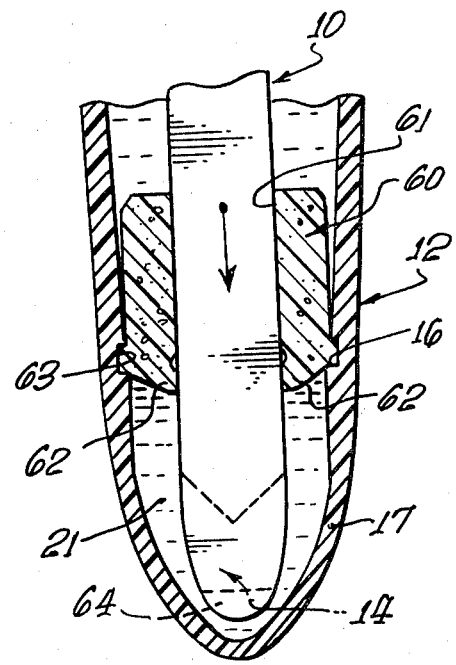
FIG. 26 is a fragmentary, cross-sectional side elevation of the test tube, strip and plug of FIG. 25 with the strip pushed to the bottom of the test tube.
Figure 28:
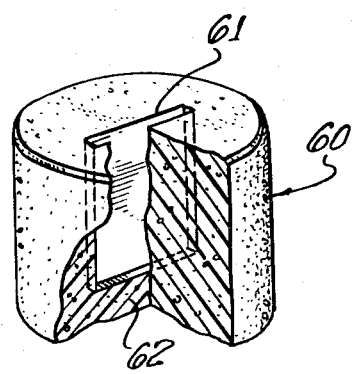
FIG. 28 is a perspective view of the plug of FIG. 25, partly broken away.

In use, the lower chamber 14 is inserted in recess 61 and a liquid-tight seal is formed between the sidewalls of the recess and the sidewalls of strip 10 so that chamber 14 remains empty. Next, the plug and strip are inserted into the test tube 12 which is filled with liquid. As plug 60 is pushed downwardly into test tube 12, the lower surface thereof touches shoulder 16 which stops the downward movement of plug 60. Further, pressure on the strip 10 forces the lower end of strip 10 through the floor 62 of plug 60 as shown in FIG. 26. This causes chamber 14 to be filled with liquid 21 which in the case of the urinalysis technique comprises the lower part on the specimen. An annular recess 63 may be formed above shoulder 16 which tends to hold plug 60 in the test tube when strip 10 is withdrawn therefrom. It is also possible that plug 60 could be formed with a ring at the lower outer edge thereof that would fit within annular recess 63.

Figure 27:
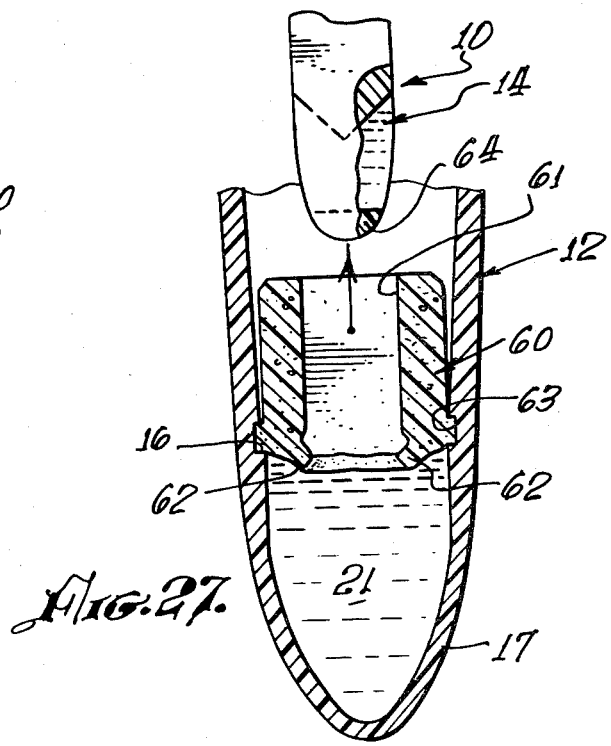
FIG. 27 is a fragmentary, cross-sectional side elevation of the test tube, strip and plug of FIG. 25 with the strip withdrawn from the plug.

The lower terminous of strip 10 is preferably solid as shown best in FIG. 27 to assist the passage of strip 10 through floor 62. This also helps assure the dimensional integrity of chamber 14.

Plug 60 may be used in the same manner as disc 11 as described above in the discussion of FIGS. 21(a), (b), (c) and (d). Thus, the upper portion of the specimen is decanted from test tube 11 leaving only the portion 21 in the lower portion 17 of test tube 12. The removal of the strip 10 through recess 61 tends to remove any excess liquid from the outside of strip 10 while capillary action continues to hold the sample within recess 14. The result is a particularly neat and trouble-free system for the further microscopic evaluation of the sample within chamber 14.

Plug 60 may be fabricated from any material which is sufficiently frangible so that strip 10 may be passed though floor 62 without damaging strip 10. Alternatively, recess 61 could be formed so that it passes completely through plug 60 and this requirement of frangibility would not be necessary. The chamber 14 of strip 10 would be held in an empty condition as long as an airtight seal was formed between the edges of strip 10 and recess 61 since water would not enter the lower part of recess 61 since there would be no way for the air to escape. In this configuration, the closed portion 64 would be necessary.

It is preferable that plug 60 be fabricated from a lightweight inexpensive material such as polystyrene foam, polyurathene foam or other polymeric or elastomeric material. It is preferable that the material of construction be slightly flexible so that it forms a tight seal against strip 10, and furthermore a slight degree of flexibility assists in forcing the plug into the annular recess 63.

Another important feature of the present invention is its ability to agitate the contents of lower portion 21 of the specimen. This is done after strip 10 has been inserted to the bottom of the test tube as shown in FIG. 5. At this point, the upper end of strip 10 may be flicked or otherwise moved causing the lower end of strip 10 to move within the lower portion 21 of the specimen. This movement causes a mixing of the particulate matter and the remaining portion of liquid sample thus obtaining a representative sample or the particulate matter for microscopic examination.

It is important that the chamber 14 be shaped in such a way so that it collects a sample without entrapping a large amount of air. This can be accomplished in various ways such as those shown in FIGS. 8 through 15 of the drawings. In FIG. 8, the chamber has a "V" shaped upper wall and has outer edges 22 and 23. When chamber 14 is inserted in a liquid sample, the air originally existing in the chamber tends to rise and pass out of the chamber at the two points indicated by reference characters 26 and 27 of FIG. 9. Similarly, chamber 14 of the device of FIGS. 10 and 11 has a slanted upper wall, and air tends to escape at the point indicated by reference character 28 in FIGS. 10 and 11. Generally, any convex shaped upper wall will prevent air entrapment.

The use of a hole to void the air may also be combined with a chamber which has side edges such as the chamber shown in FIGS. 14 and 15. Chamber 14 has side edges 30 and 31 which would tend to trap air if it were not for the presence of hole 32. Edges 30 and 31 are useful in holding an accurate inner dimension between the outer edges 22 and 23 of chamber 14. Hole 32 may be formed in only one of two of the outer edges 22 and 23 or in both edges 22 and 23. A hole diameter of about 0.02 inches has been found satisfactory.

The reagent pads 13 may be held to strip 10 by an adhesive such as shown in FIGS. 8 and 10 of the drawings or by the use of a porous mesh 33 as shown in FIG. 12 of the drawings. Alternatively, the reagent pads may be held by an opening in strip 10 as shown in FIGS. 14 and 16 of the drawings. In any event, it is useful that the reagent pads be held securely to strip 10 to reduce the possibility of a mix-up in the samples.

One method of fabricating the strip of the present invention is shown in FIGS. 17 through 20 of the drawings. Strip 10 may be formed from three separate transparent strips 40, 41 and 42. It is not essential that strip 41 be transparent although, this is a preferred form of the present invention in that the reagent strips are typically most accurately read over a transparent background. However, if strip 41 were white, the color reading of the strips might be altered and for some, applications could be enhanced.

Many strips may be cut from a single lamination such as that shown in FIG. 20. A transparent bottom layer 42 is laminated to two middle layers 41 and 43 and a top layer 40. A plurality of treated strips 13 are adhered to the upper surface of layer 40 and the entire sheet is laminated preferably in a press to result in a firm lamination. Conventional adhesives may be used of a type which would not interfere with the test results. Top layer 40 and bottom layer 42 should be fabricated from a clear plastic which is not too hydrophobic. Instead, the polymer should have an affinity for water so that the specimen will tend to be drawn into the chamber instead of being repelled therefrom. Preferred plastics include cellulose ester compositions such as cellulose acetate and cellulose acetate butyrate such as that sold under the trademark "Tenite" by Eastman Chemical Products, Inc.

After the lamination is complete, the strips may be readily cut from the laminated unit by a conventional die. The finished strip is shown in cross-sectional view in FIG. 18 where bottom layer 42 is adjacent to middle layer 41, top layer 40 and pad 13. The thickness of middle layer 41, of course, determines the width of chamber 14 as shown best in FIG. 19. Chamber 14 should be narrow enough to assure fluid entry by capillary action and yet not be so narrow as to prevent the entry of particulate matter or to prevent the entry of sufficient particles for meaningful microscopic evaluation. The range of acceptable spacing is between 0.0005 and 0.025 of an inch, and the optimum range is 0.002 to 0.008 of an inch with about 0.004 being recommended and preferred.

Instead of lamination, the strips of the present invention may be injection molded. Chamber 14 may either be formed in the injection molding process or may be cut in the finished strip. Alternatively, the chamber 14 may be cut from a strip which has been cut from a larger sheet similar to that shown in FIG. 20 except the sheet would be a solid integral sheet and not laminated.

The disc 11 not only holds the bottom portion 21 of the specimen in the test tube as shown best in FIG. 21(c), but also serves to hold the strip 10 in a position to be viewed, by a microscope as shown best in FIG. 22. A jig 50 has a semi-circular slot 51 and an opening 52. Disc 11 which holds strip 10 is inserted in slot 51 so that chamber 14 is held above opening 52. Jig 50 is moved so that opening 52 is below microscope 53 which may then easily be used to view the contents of chamber 14. It should be noted that the liquid is held in chamber 14 by capillary action so that after strip 10 has been withdrawn from the sample, the portion of the specimen in chamber 14 does not turn out of the chamber but instead is held therein. For embodiments where the disc 11 or plug 60 remains in test tube 12, other means may be used to hold strip 10 such as a clamp.

A substantial advantage of the use of the device of the present invention is that the viewing by microscope may be done without any separate specimen transferring step thereby eliminating a possible source of sample mix-up. The test pads 13 are an integral part of strip 10 and therefore the chance of error is reduced to a very low level.

The thickness of top layer 40 and bottom layer 42 is not critical, but at least one of the layers should have sufficient flexibility so that it is deformed by passage through slot 15 if a disc is used. Where a plug is used, no flexibility is necessary. The thickness of the disc should be sufficient so that it is held by shoulder 16 of test tube 12 and moves upwardly along strip 10 as strip 10 is inserted to the bottom of test tube 12 as shown in FIGS. 21(b) and 21(d).

The device of the present invention may be made economically enough so that it is disposable. The device requires a minimum of peripheral apparatus other than a microscope.

The test pads may be held to strip 10 by inserting the same through an opening in the strip as shown in FIGS. 14 and 16. There the reagent pad 13 is made of a sufficient thickness so that it may be held in strip 10 by opening 55 formed therein.

While the bottom of strip 10 has been shown as formed in a rounded configuration which generally conforms to the bottom of test tube 12, it is not necessary that the strip be so shaped. It could instead be rectangular, pointed or otherwise shaped.

The present embodiments of this invention are thus to be considered in all respects as illustrative and not restrictive, the scope of the invention being indicated by the appended claims rather than by the foregoing description. All changes which come within the meaning and range of equivalency of the claims therefore are intended to be embraced therein.

What is claimed is:

1. A device for facilitating the microscopic viewing of liquid specimens, said device comprising:
    an elongated strip having a sampling and viewing chamber at the lower extremity thereof, said chamber being formed by two generally parallel transparent flat members which are spaced close enough together to be filled by capillary action and said chamber being sufficiently open to permit it to be filled when immersed in a liquid;
    a strip supporting member having an opening formed therein for insertion of the lower extremity of said elongated strip, said opening being small enough so that the strip supporting member is firmly held by said strip after the strip is inserted therein; and
    test tube means having means for limiting the downward movement of the strip supporting member formed near the bottom thereof, said test tube means being large enough to permit the insertion of the strip and strip supporting member therein and said means for limiting being large enough to permit the insertion of the lower end of the strip but being configured to prevent the passage of the strip supporting member past the shoulder and instead to hold the strip supporting member thereon and to form a generally waterproof barrier between the inner wall of the test tube means and the strip supporting member, whereby liquid located below said strip supporting member will be held in said test tube means when said strip supporting member is held in its lowermost position in said test tube means; and means preventing liquid flow into said sampling and viewing chamber until said strip supporting member contacts said means for limiting the downward movement.

2. The device of claim 1 wherein the chamber has a thickness of between 0.0005 and 0.025 inches.

3. The device of claim 1 wherein said chamber has a thickness of between 0.002 and 0.008 inches.

4. The device of claim 1 wherein said chamber has a thickness of about 0.004 inches.

5. The device of claim 1 wherein said strip supporting member comprises a disc.

6. The device of claim 5 wherein said disc has a slot which is narrowed in the center.

7. The device of claim 1 wherein said strip is fabricated by laminating three layers of material together, the outer two layers being transparent and the center layer being equal to the thickness of said chamber and said center layer terminating at a distance spaced from the terminous of said strip thereby forming a chamber between the outer two layers.

8. The device of claim 1 wherein said chamber has a "V" shaped upper edge.

9. The device of claim 1 wherein said chamber has a generally straight upper end positioned at a slant with respect to the horizontal.

10. The device of claim 1 further including a small opening through at least one of said flat members of said chamber near the upper terminous of said chamber.

11. The device of claim 1 wherein said chamber has at least one side edge extending downwardly from the upper terminous of the chamber and positioned adjacent the side edges of the strip whereby the transparent flat members are maintained in a parallel position with respect to one another.

12. The device of claim 1 further including at least one reagent pad held to the side of said elongated strip.

13. The device of claim 12 wherein said reagent pad is held to said elongated strip by an adhesive.

14. The device of claim 12 wherein said reagent pad is held to said strip by a porous mesh.

15. The device of claim 12 wherein said reagent pad is held in an opening formed through said elongated strip.

16. The device of claim 5 further including a jig having disc-supporting means associated therewith.

17. The device of claim 16 wherein said disc-supporting means comprises a slot formed in said jig.

18. The device of claim 17 wherein said slot is a semi-circular slot.

19. The device of claim 5 wherein said means preventing liquid flow comprises a waterproof layer positioned on the lower surface of said disc, said layer being penetratable by said strip.

20. The device of claim 1 wherein said strip supporting member is a plug having a recess formed therein.

21. The device of claim 20 wherein said means preventing liquid flow comprises a floor located at the bottom of said plug to prevent the entry of liquid into the recess from the bottom surface of said plug.

22. The device of claim 20 including a recess formed in the inner surface of said test tube for holding a lower terminous portion of said plug.

23. The device of claim 1 wherein said chamber has a solid lower terminous.

24. A method for performing a urinalysis test on a specimen of urine comprising the steps of:
placing a specimen in a test tube having an inner stop means positioned near the bottom thereof;
centrifuging the specimen;
placing an elongated strip having a chamber formed by two generally parallel transparent flat members at the lower extremity thereof, said flat members being close enough together to be filled by capillary action and said chamber being sufficiently open to permit it to be filled when immersed in a liquid, through a strip supporting member having a recess formed therein, said strip being small enough to fit to the bottom of said test tube and said strip supporting member being of a size and shape to permit entry into said test tube but to be held by the stop means of said test tube;
inserting said strip and strip supporting member into said centrifuged sample until said strip supporting member rests on said stop means, said chamber not being open to the contents of the test tube at this time;
decanting that portion of the specimen held above said strip supporting member while maintaining that portion of the specimen held below said strip supporting member;
agitating the remaining liquid in the test tube to suspend any solid particles contained therein;
pushing downwardly on said strip and opening said chamber to the contents of the test tube held below the strip supporting member until the bottom of said strip is positioned near the bottom of the test tube; and
removing said strip from said test tube and viewing the sample held within the chamber of said strip.

25. The method of claim 20 wherein said strip supporting member is a disc.

26. The method of claim 20 wherein said stop means comprises a shoulder formed in the inner surface of said test tube.

27. The method of claim 24 further including the step of inserting said disc in a disc holding member comprising a jig positioned so that the chamber of said strip is in the viewing field of a microscope.

28. The method of claim 27 wherein the step of inserting said disc comprises inserting said disc into a semi-circular slot in said jig.

29. The method of claim 19 wherein said strip supporting member is a plug having a recess formed therein, said recess having about the same cross-sectional size as the cross-sectional size of said elongated strip whereby when said elongated strip is removed from said plug, the exterior of said elongated strip is wiped dry.

* * * * *